(12) United States Patent
Guo et al.

(10) Patent No.: US 8,956,300 B2
(45) Date of Patent: Feb. 17, 2015

(54) METHOD AND DEVICE FOR NEEDLE VISUALIZATION

(75) Inventors: Jianjun Guo, Wuxi (CN); Menachem Halmann, Milwaukee, WI (US); Jonathan Alan Bowman, Montgomery, AL (US); Jiajiu Yang, Wuxi (CN)

(73) Assignee: General Electric Company, Schenectady, NY (US)

( * ) Notice: Subject to any disclaimer, the term of this patent is extended or adjusted under 35 U.S.C. 154(b) by 89 days.

(21) Appl. No.: 13/436,086

(22) Filed: Mar. 30, 2012

(65) Prior Publication Data
US 2013/0261432 A1 Oct. 3, 2013

(30) Foreign Application Priority Data

Mar. 31, 2011 (CN) .......................... 2011 1 0093514

(51) Int. Cl.
*A61B 8/00* (2006.01)
(52) U.S. Cl.
USPC ........................................ 600/447
(58) Field of Classification Search
CPC ............... A61B 8/0841; A61B 8/4209; A61B 2017/3413; A61B 10/0233; A61B 2019/5276; A61B 2019/5425
USPC ......... 600/437, 443, 447, 461, 463, 467, 471; 128/916
See application file for complete search history.

(56) References Cited

U.S. PATENT DOCUMENTS

| | | | |
|---|---|---|---|
| 3,556,079 A | 1/1971 | Omizo et al. | |
| 4,249,539 A | 2/1981 | Vilkomerson et al. | |
| 4,407,294 A | 10/1983 | Vilkomerson et al. | |
| 4,428,379 A | 1/1984 | Robbins et al. | |
| 4,431,006 A | 2/1984 | Trimmer et al. | |
| 4,869,259 A | 9/1989 | Elkins | |
| 4,977,897 A | 12/1990 | Hurwitz | |
| 5,095,910 A | 3/1992 | Powers | |
| 2002/0173719 A1* | 11/2002 | Zhao et al. | 600/437 |
| 2009/0137904 A1* | 5/2009 | Wu et al. | 600/447 |
| 2013/0072785 A9* | 3/2013 | Guo et al. | 600/424 |

FOREIGN PATENT DOCUMENTS

EP 0952462 A2 10/1999
EP 1132049 A1 9/2001

OTHER PUBLICATIONS

Kurohiji et al., "Motion marking in color Doppler ultrasound needle and catheter visualization", J Ultrasound Med 1990, vol. 9, pp. 243-245.
Uhercik et al., "Multi-resolution parallel integral projection for fast localization of a straight electrode in 3D ultrasound images", ISBI 2008 pp. 33-36.

* cited by examiner

*Primary Examiner* — Elmer Chao
(74) *Attorney, Agent, or Firm* — GE Global Patent Operation; Marc A. Vivenzio

(57) ABSTRACT

A method for needle visualization for an ultrasound imaging device, the method comprising alternately acquiring a tissue frame followed by a needle frame at a temporal spacing to form a frame sequence, spatially compounding the frame sequence, and outputting an image frame resulting from spatial compounding.

10 Claims, 5 Drawing Sheets

METHOD AND DEVICE FOR NEEDLE VISUALIZATION

BACKGROUND OF THE INVENTION

1. Field of the Invention

Embodiments of the present invention generally relate to medical ultrasound imaging and, more particularly, to a method and a device for needle visualization.

2. Description of the Prior Art

Since an ultrasound imaging device can provide clear images of human blood vessels and blood flow and is particularly useful as a positioning and aiding tool in procedures such as cardiac invasive therapy, the device enables a physician to discern a lesion site of a patient and each progress of the procedure and is thus crucial to the success of operations.

For procedures demanding invasion into nerves and blood vessels, needle probing and visualization of real-time and high-quality needle images are paramount. Therefore, there exists a need for an ultrasound imaging device to display images of a travelling needle in a real time and high quality fashion.

Existing needle visualization techniques for the ultrasound imaging system mainly include B steer, SteerXBeam, Expanded SteerXBeam and the like. Examples of such needle visualization techniques: provide an ultrasound transducer in a needle; include the use of a Doppler method; include techniques for modifying needles to enhance acoustic reflection; provide an electro-magnetic device attached to the needle tip; include techniques that reveal image analysis based on amplitude information; include techniques for the adjustment of scan angles; and include a scan technique of needle visualization.

Existing techniques typically add an additional frame for detecting the needle (hereinafter referred to as a needle frame) to human tissue frames (hereinafter referred to as tissue frames). For example, display of every five tissue frames is followed by display of one needle frame. Although said techniques can present needle images in ultrasound images, there is a delay in the display of needle images. In other words, after an operation of the needle, the physician has to wait for a period of time until a current location of the needle in the human body is displayed in the ultrasound images.

BRIEF SUMMARY OF THE INVENTION

According to an embodiment of the present invention, there is provided a method for needle visualization for an ultrasound imaging device. The method comprises alternately acquiring a tissue frame followed by a needle frame at a temporal spacing to form a frame sequence, spatially compounding the frame sequence, and outputting an image frame resulting from spatial compounding.

According to another embodiment of the present invention, there is provided a device for needle visualization for ultrasound imaging. The device comprises a mechanism configured to alternately acquire a tissue frame followed by a needle frame at a temporal spacing to form a frame sequence, a mechanism configured to spatially compound the frame sequence, and a mechanism configured to output an image frame resulting from spatial compounding.

BRIEF DESCRIPTION OF THE DRAWINGS

Embodiments of the present invention will be more apparent to those skilled in the art upon reading the following description with reference to the accompanying drawings, in which.

DETAILED DESCRIPTION OF THE INVENTION

The present invention will be described in detail by way of specific embodiments. However, it should be understood that the present invention is not limited to these specific embodiments.

Figure 1:
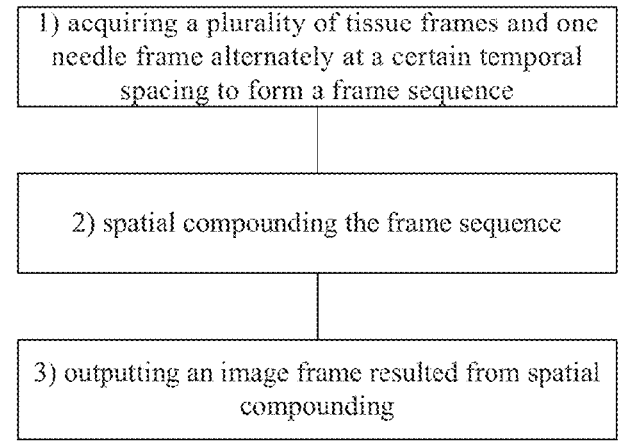
FIG. 1 depicts a flow chart according to an embodiment of the prior art method for needle visualization.

The prior art technical solution is first introduced here for clarity. As shown in FIG. 1, the prior art technical solution comprises the following steps: (1) acquiring a plurality of tissue frames and one needle frame alternately at a certain temporal spacing to form a frame sequence; (2) spatial compounding the frame sequence; and (3) outputting an image frame resulted from spatial compounding, wherein the plurality generally comprises, for example, three tissue frames obtained through scanning at 0 degree, 15 degrees, and −15 degrees respectively. This is only an example, while scans may be performed at any other angle.

It should be noted that it is also feasible to acquire four, five, or any other number of, tissue frames followed by one needle frame.

Figure 2:
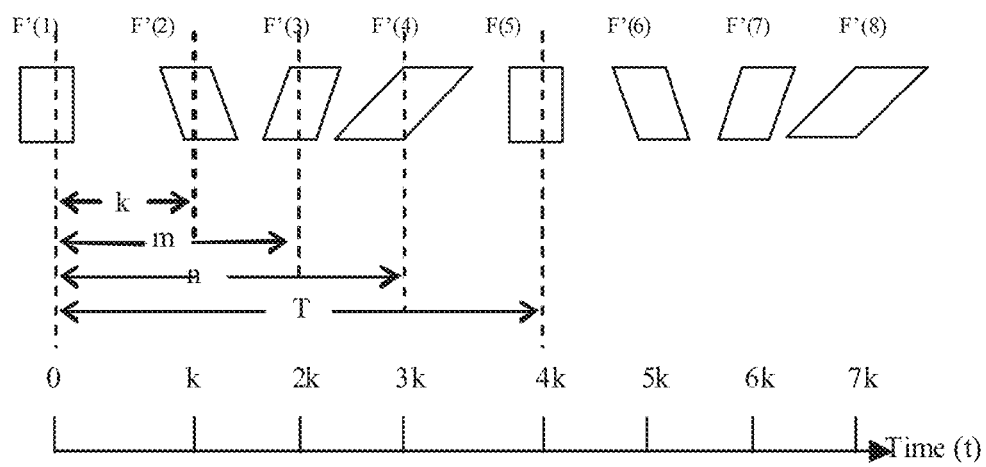
FIG. 2 illustrates a frame sequence obtained according to an embodiment of the prior art.

As shown in FIG. 2, the tissue is scanned at three regular angles, 0 degree, 10 degrees, −10 degrees, thus obtaining tissue frames (denoted in terms of angles) 0, +10, −10,0, +10, −10, . . . 0, +10, −10, . . . , where 0 represents a tissue frame obtained by scanning at an angle of 0 degree, +10 a tissue frame obtained by scanning at a steered angle of 10 degrees, and −10 a tissue frame resulting from scanning at a steered angle of −10 degrees. In the anatomical space, the needle frame is obtained by scanning at an angle different from those adopted for tissue frames. As illustrated in FIG. 2, an angle of +20 is adopted for the needle frames.

The frame sequence in FIG. 2 comprises F'(1), F'(2), F'(3), F'(4), F'(5), . . . F'(i), . . . . Next, spatial compounding is performed on every number of frames, wherein the number may be three, four, five, etc. If the number equals three, spatial compounding is conducted on F'(1), F'(2) and F'(3), then on F'(2), F'(3) and F'(4), and thereafter on F'(3), F'(4) and F'(5), . . . , thus running the spatial compounding in turn. If the number equals four, spatial compounding is conducted on F'(1), F'(2), F'(3) and F'(4), then on F'(2), F'(3), F'(4) and F'(5), and thereafter on F'(3), F'(4), F'(5) and F'(6), . . . , thus running the spatial compounding in turn. Subsequent to the spatial compounding, the resultant image frames are output to an ultrasound imaging device for display to a physician.

As is also apparent from FIG. 2, the frame sequence comprises in turn an unsteered tissue frame, a right steered tissue frame, a left steered tissue frame, a large angle needle frame, etc. The temporal spacing between the frames is equivalent. That is, frames are acquired at a fixed temporal spacing, such as k millisecond as in this embodiment.

As is further shown in FIG. 2, assuming the temporal spacing between an unsteered tissue frame and an adjacent left-steered tissue frame is m, the temporal spacing between the unsteered tissue frame and a closest needle frame is n, and the temporal spacing between two adjacent unsteered tissue frames is T, then m=2 k, T=4 k, and n=3 k.

As such, ignoring steering directions, the frame rate would be 1/k Hz, while the needle frame rate is 1/n=1/3 k Hz, thus giving rise to needle display delay in ultrasound images.

Figure 3:
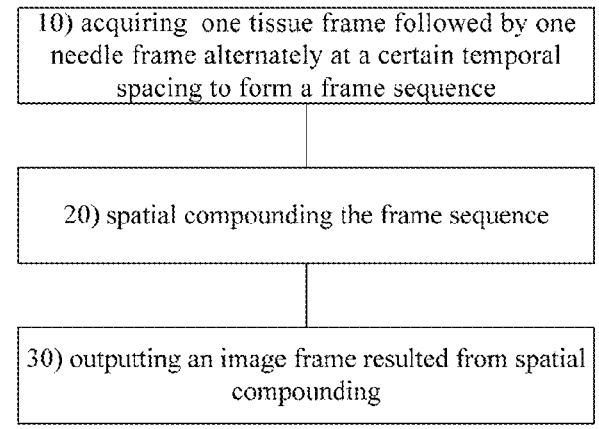
FIG. 3 shows a flow chart according to an embodiment of the present invention.

As illustrated in FIG. 3, according to one embodiment of the present invention, a method for needle visualization is disclosed. The method comprises (10) acquiring one tissue frame followed by one needle frame alternately at a certain temporal spacing to form a frame sequence; (20) spatially compounding the frame sequence; and (30) outputting an image frame resulting from the spatial compounding.

As is seen, the frame sequence formed according to the method for needle visualization comprises one tissue frame, one needle frame, one tissue frame, one needle frame . . . . Ignoring steering directions, the temporal spacing between two closest needle frames equals the temporal spacing between two closest tissue frames, and therefore, the frame rate for tissue frames is equal to that for needle frames, thereby eliminating needle frame delay found in prior art methods for needle visualization.

In one embodiment, a plurality of tissue frames are acquired at a plurality of regular angles for a same anatomical space, and then compounded, such that image noise can be suppressed.

In one embodiment, each needle frame is acquired at an angle greater than all the regular angles for acquiring tissue frames. Alternatively, it is preferable that the angle for the needle frame is approximately perpendicular to a penetrating angle of the needle, such that a high quality image of the needle can be obtained.

All the above-mentioned angles refer to angles along a same scanning direction.

For example, a same anatomical space (i.e., a same position in a human body) is scanned at three regular angles along a same scanning direction, such as 0 degree, +10 degrees, −10 degrees, to obtain tissue frames. Or, a same anatomical space is scanned at five regular angles, such as 0 degree, +10 degrees, −10 degrees, +15 degrees, −15 degrees, to obtain tissue frames. The number of regular angles and the degree of regular angles are freely selectable according to circumstances.

In one embodiment, step (20) further comprises selecting a number of sequential frames in turn within the frame sequence; and averaging values at a same position in the number of sequential frames.

In an alternative embodiment, step (20) may further comprise selecting a number of sequential frames in turn within the frame sequence; and selecting a maximum from values at a same position in the number of sequential frames.

The objective of step (20) is primarily for removing noise. Regarding spatial compounding, there is already a plurality of known techniques.

To avoid the resulting image being over-enhanced, gradual enhancement along the depth may be adopted, where the depth refers to the scan depth of the ultrasound probe. Step (20) may also be implemented as follows: selecting a number of sequential frames in turn within the frame sequence; spatially compounding tissue frames within the number of sequential frames to form a new tissue frame; and selecting values at a same position in a needle frame and the new tissue frame according to a ratio increasing with depth, and then summing the values.

As is seen, firstly, tissue frames within a certain number of sequential frames are spatially compounded to form a new tissue frame. Next, values of pixel points at a same position in a needle frame and the tissue frame are selected according to a ratio. For example, at a depth of 1-2 cm, a ratio of 3:7 may apply. That is, 30% of a value of a pixel point at a same position of a needle frame, and 70% of a value of a pixel point at the same position of the new tissue frame, are selected and then summed. The ratio of 3:7 is illustrative only and other ratios may be adopted.

"Increasing with depth" means that if the depth increases to 3 cm, the ratio between values at a same position in a needle frame and a tissue frame should be greater than the ratio in case of a depth of 1-2 cm. For example, if a ratio of 3:7 is adopted for the depth of 2 cm, the ratio in case of a depth of 3 cm shall be greater than 3:7, for example, a ratio of 4:6, etc.

In case of a depth of 5 cm or more, only the value of the needle frame is adopted, while the value of the tissue frame will be ignored. That is, the value for the corresponding pixel point of the needle frame is taken at a percentage of 100, such that lower enhancement is obtained.

Alternatively, the number of sequential frames includes a plurality of tissue frames and a plurality of needle frames. The needle in the image frame obtained by spatially compounding a number of tissue frames and a number of needle frames in a sequence is often not clear enough. As such, spatial compounding may also be conducted on a plurality of tissue frames and one latest needle frame, such that the needle in the image frame is clearly discernable.

The method for needle visualization according to an embodiment of the present invention will be explained in detail below by way of example of an invasive procedure on the nerves.

Figure 4:
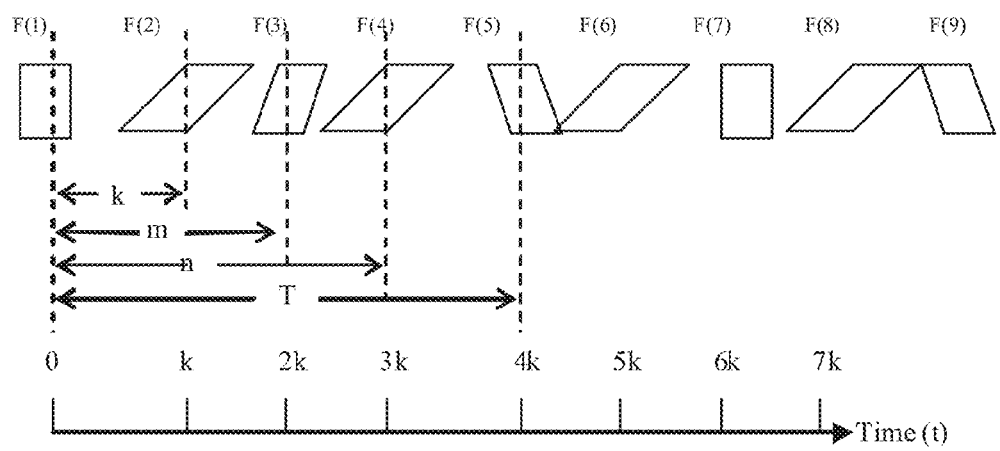
FIG. 4 illustrates a frame sequence obtained according to an embodiment of the present invention.

FIG. 4 depicts a frame sequence obtained according to an embodiment of the method for needle visualization. In this embodiment, tissue frames are obtained by scanning at three regular angles, 0 degree, +10 degrees, −10 degrees; needle frames are obtained by scanning at a steered angle of 20 degrees. In the embodiment, the temporal spacing between two frame acquisitions is designated as k and the initial acquiring time as 0.

As shown in FIG. 4, the frame sequence comprises F(1), F(2), F(3), F(4), F(5), . . . F(i), . . . , wherein F(1) represents a tissue frame acquired at an angle of 0 degree and at a time point of 0, F(2) is a needle frame acquired at a 20 degrees steered angle at a time point of k, F(3) is a tissue frame acquired at an angle of +10 degrees and at a time point of 2 k, F(4) is a needle frame acquired at a 20 degrees steered angle at a time point of 3 k, F(5) is a tissue frame acquired at an angle of −10 degrees and at a time point of 4 k, F(6) is a needle frame acquired at a 20 degrees steered angle at a time point of 5 k, F(7) is a tissue frame acquired at an angle of 0 degree and at a time point of 6 k . . . . The temporal spacing from the acquisition of tissue frame at 0 degree to the next acquisition of tissue frame at 0 degree can be called a period of T, which equals 6 k in the present embodiment.

Figure 5:
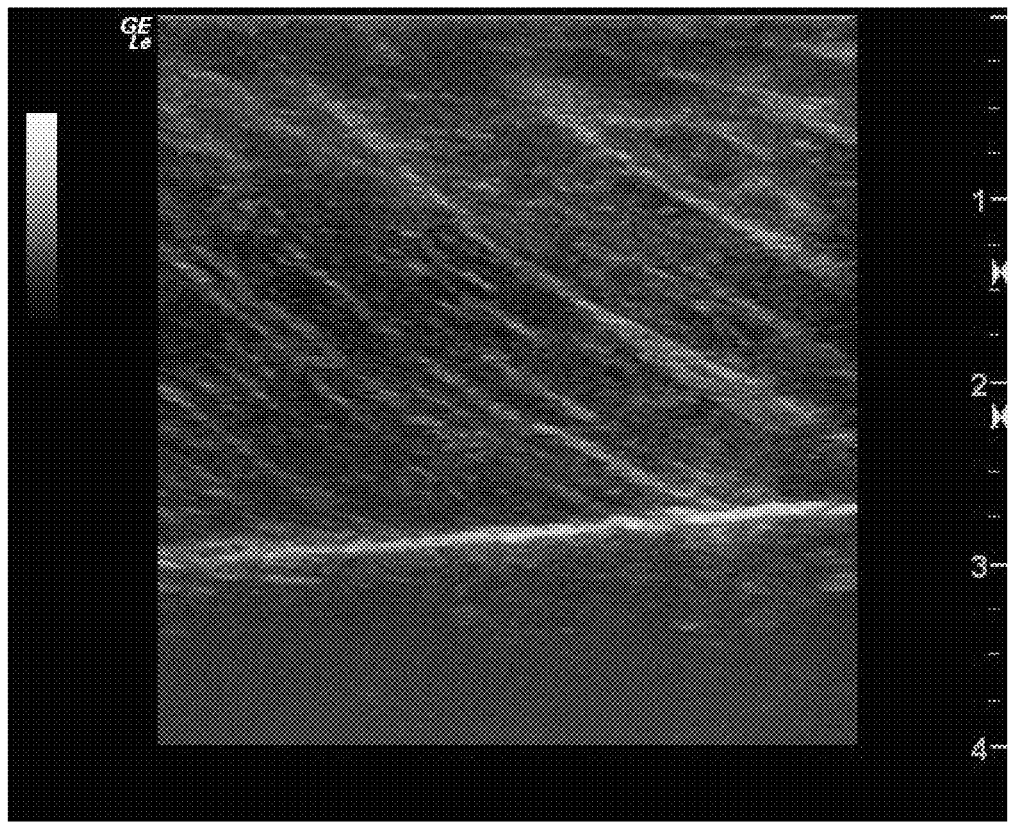
FIG. 5 is a diagram of a tissue frame acquired according to an embodiment of the present invention.
Figure 6:
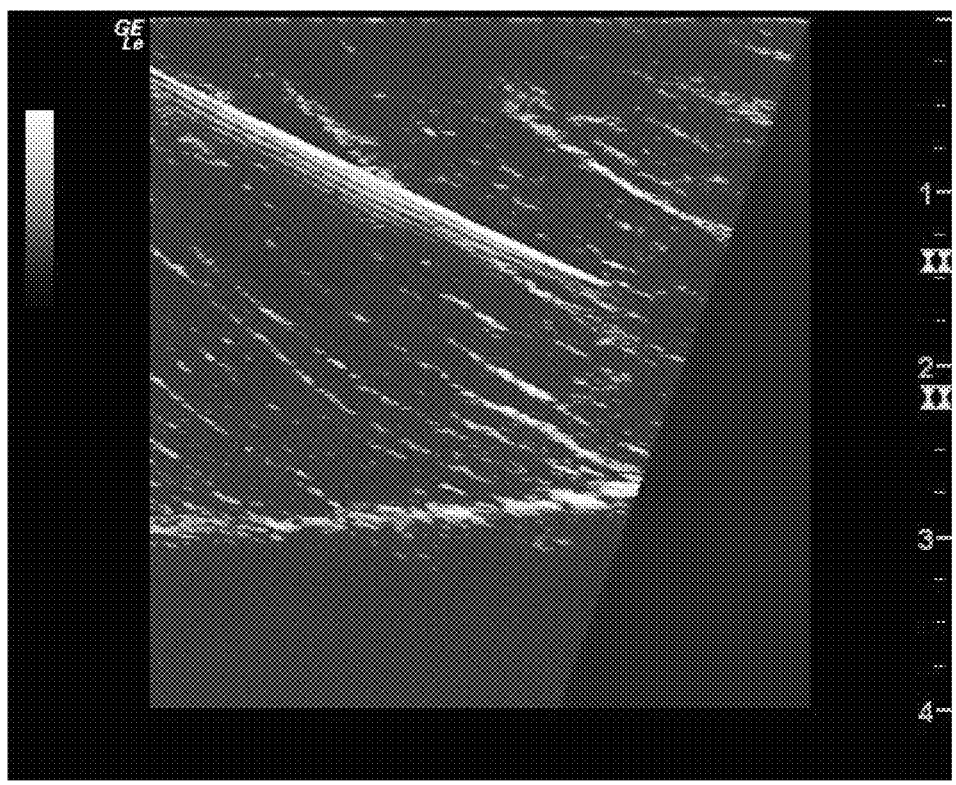
FIG. 6 is a diagram of a needle frame acquired according to an embodiment of the present invention.

FIG. 5 depicts a captured tissue frame acquired at 0 degree at a first time point, while FIG. 6 shows a needle frame scanned at a large angle at a second time point. Since the penetrating angle of the needle is large, the tissue frame contains no information as to the needle. For the needle frame, since the scan angle is approximately perpendicular to the penetrating angle of the needle, a needle image of fairly good quality is seen in the needle frame.

Next, spatial compounding is performed on the frame sequences in turn, each of which may comprise six successive frames. For example, F(1), F(2), F(3), F(4), F(5) and F(6) are first spatially compounded, F(2), F(3), F(4), F(5), F(6) and F(7) are then spatially compounded, etc. In other words, among the six successive frames for each spatial compounding, there are three tissue frames and three needle frames. However, the three needle frames are acquired at a same steered angle but at different time points. If these three needle frames are compounded, tailing will occur. As such, in the embodiment, the two needle frames that are first acquired will be discarded, and only the latest needle frame is retained. As such, four frames are spatially compounded. If shown by angles, the sequence is 0, +10, −10, +20; +10, −10, +20, 0; . . . ; 0, +10, −10, +20; . . . . The sequence may also be expressed as F(1), F(3), F(5), F(6); F(3), F(5), F(6), F(7); . . . .

Figure 7:
FIG. 7 is a diagram of an image frame output according to an embodiment of the present invention.

In the embodiment, averaging is adopted. Values at a same position in F(1), F(3), F(5), F(6) are averaged to obtain an image frame which is then output, whereafter values at a same position in F(3), F(5), F(6), F(7) are averaged to obtain another image frame which is then output, . . . , thus running the averaging in turn. FIG. 7 is a diagram of a captured image frame output after spatial compounding, wherein display of the needle in the tissue is enhanced without compromising the tissue images.

Table 1 below shows the test results for the prior art and an embodiment of the present invention. "Data rate" in Row 1 refers to data update rate for the front end scanning of the ultrasound system, while Row 2 provides the actual processing rate at the rear end of the system. Rows 3 and 4 list the test data for embodiments of the present invention and the prior art respectively at a same data rate. Row 5 provides the ratio between needle frame refreshing rates of embodiment of the present invention and the prior art. As is apparent, the refreshing rate of needle frames by embodiments of present invention improves significantly. When the data rate is 15 frames/second or 20 frames/second, the needle frame refreshing rate for embodiments of the present invention is 1.86 or 1.97 times as much as that of the prior art; when the data rate is 25, 30, or 36, the needle frame refreshing rate for embodiments of the present invention is 2 times as much as that of the prior art.

In said device, a plurality of tissue frames are acquired at a plurality of regular angles for a same anatomical space.

In said device, each needle frame is acquired at an angle greater than all the regular angles for acquiring the plurality of tissue frames.

In one embodiment, the means for spatial compounding may further comprises means for selecting a number of sequential frames in turn within the frame sequence; and means for averaging values at a same position in the number of sequential frames.

In another embodiment, the means for spatial compounding may comprise means for selecting a number of sequential frames in turn within the frame sequence; and means for selecting a maximum from values at a same position in the number of sequential frames.

In another embodiment, the means for spatial compounding may further comprise means for selecting a number of sequential frames in turn within the frame sequence; means for spatially compounding tissue frames within the number of sequential frames to form a new tissue frame; and means for selecting values at a same position in the needle frame and the new tissue frame according to a ratio increasing with depth and summing the values, said depth referring to scan depth of an ultrasound probe.

The number of sequential frames includes a plurality of tissue frames and a plurality of needle frames. Alternatively, the number of sequential frames may include a plurality of tissue frames and one latest needle frame.

Since the device for needle visualization according to an embodiment of the present invention corresponds to the present method for needle visualization, no elaboration of the device will be provided hereinbelow.

In summary, embodiments of the present invention obtain a frame sequence by acquiring one tissue frame followed by one needle frame in a repeated manner, such that uniform spacing is achieved between needle frames and tissue frames, and real time display of the needle is realized.

TABLE 1

| | | | | | | |
|---|---|---|---|---|---|---|
| Data rate (frames/second) | | 15 | 20 | 25 | 30 | 36 |
| Frame rate (frames/second) | | 11 | 13 | 16 | 20 | 20 |
| Method for needle visualization of an embodiment of the present invention | Total frames update/minute | 667 | 813 | 971 | 1254 | 1211 |
| | Needle frames update/minute | 358 | 470 | 590 | 713 | 844 |
| | Needle frame rate/second | 5.97 | 7.83 | 8.44 | 11.88 | 14.07 |
| Prior art methods | Total frames update/minute | 624 | 816 | 975 | 1325 | 1215 |
| | Needle frames update/minute | 180 | 240 | 296 | 360 | 424 |
| | Needle frame rate/second | 3.00 | 4.00 | 4.93 | 6.00 | 7.04 |
| Comparison between the embodiments of the present invention and the prior art (the ratio of the embodiments of the present invention to the prior art) | | 1.86 | 1.97 | 2.00 | 2.09 | 2.00 |

According to another embodiment of the present invention, a device for needle visualization for an ultrasound imaging device is provided, the device comprising means for acquiring one tissue frame followed by one needle frame alternately at a certain temporal spacing to form a frame sequence; means for spatially compounding the frame sequence; and means for outputting an image frame resulting from the spatial compounding.

Moreover, embodiments of the present invention select values at a same position in the needle frame and the new tissue frame according to a ratio increasing with depth, such that noise is suppressed, and quality of tissue images is guaranteed.

While the present invention has been described above in terms of specific embodiments with reference to the drawings, it will be understood by those skilled in the art that various changes, modifications, and substitutions may be made without departing from the spirit and scope of the present invention, which changes, modifications, and substitutions will all fall within the spirit and scope defined by the appending claims.

What is claimed is:

1. A method for needle visualization, the method comprising:
   using an ultrasound imaging device having an ultrasound probe to perform an ultrasound scan by:
      forming a frame sequence from the ultrasound scan comprising a plurality of tissue frames having no information as to a needle and a plurality of needle frames having a needle image by alternately acquiring one tissue frame followed by one needle frame, wherein the frame sequence has a frame rate for the plurality of tissue frames that is equal to the frame rate for the plurality of needle frames to achieve uniform spacing between needle frames and tissue frames, and wherein the plurality of needle frames have a scanning angle greater than all tissue frame scanning angles;
      spatially compounding the frame sequence; and
      outputting an image frame resulting from spatial compounding,
   wherein spatially compounding the frame sequence further comprises:
      selecting a number of sequential frames in turn within the frame sequence;
      spatially compounding tissue frames within the number of sequential frames to form a new tissue frame; and
      selecting values of pixel points at a same position in the needle frame and the new tissue frame according to a ratio between a percentage of the value of the pixel point in the needle frame and a percentage of the value of the pixel point in the new tissue frame, wherein the ratio between the percentage of the value of the pixel point in the needle frame and the percentage of the value of the pixel point at the same location in the new tissue frame increases with depth, and
      summing the values, wherein the depth is the scan depth of an ultrasound probe.

2. The method for needle visualization according to claim 1, wherein spatially compounding the frame sequence further comprises:
   selecting a number of sequential frames in turn within the frame sequence; and
   averaging values at a same position in the number of sequential frames.

3. The method for needle visualization according to claim 1, wherein spatially compounding the frame sequence further comprises:
   selecting a number of sequential frames in turn within the frame sequence; and
   selecting a maximum from values at a same position in the number of sequential frames.

4. The method for needle visualization according to claim 2, wherein the number of sequential frames includes frames of the plurality of tissue frames and frames of the plurality of needle frames.

5. The method for needle visualization according to claim 2, wherein the number of sequential frames includes frames from the plurality of tissue frames and one latest needle frame.

6. A device for needle visualization for ultrasound imaging, the device comprising:
   a mechanism configured to form a frame sequence from the ultrasound scan comprising a plurality of tissue frames having no information as to a needle and a plurality of needle frames having a needle image by alternately acquiring one tissue frame followed by one needle frame, wherein the frame sequence has a frame rate for the plurality of tissue frames that is equal to the frame rate for the plurality of needle frames to achieve uniform spacing between needle frames and tissue frames, and wherein the plurality of needle frames have a scanning angle greater than all tissue frame scanning angles;
   a mechanism configured to spatially compound the frame sequence; and
   a mechanism configured to output an image frame resulting from spatial compounding,
   wherein the mechanism configured to spatially compound the frame sequence is further configured to;
   select a number of sequential frames in turn within the frame sequence;
   spatially compound tissue frames within the number of sequential frames to form a new tissue frame; and
   select values of pixel points at a same position in the needle frame and the new tissue frame according to a ratio between a percentage of the value of the pixel point in the needle frame and a percentage of the value of the pixel point in the new tissue frame, wherein the ratio between the percentage of the value of the pixel point in the needle frame and the percentage of the value of the pixel point at the same location in the new tissue frame increases with depth, and
   sum the values, wherein the depth is the scan depth of an ultrasound probe.

7. The device for needle visualization according to claim 6, wherein the mechanism configured to spatially compound the frame sequence is further configured to:
   select a number of sequential frames in turn within the frame sequence; and
   average values at a same position in the number of sequential frames.

8. The device for needle visualization according to claim 6, wherein the mechanism configured to spatially compound the frame sequence is further configured to:
   select a number of sequential frames in turn within the frame sequence; and
   select a maximum from values at a same position in the number of sequential frames.

9. The device for needle visualization according to claim 7, wherein the number of sequential frames includes frames from the plurality of tissue frames and a plurality of needle frames.

10. The device for needle visualization according to claim 7, wherein the number of sequential frames includes frames from the plurality of tissue frames and one latest needle frame.

* * * * *